(12) United States Patent
Chan et al.

(10) Patent No.: US 7,935,714 B2
(45) Date of Patent: May 3, 2011

(54) COMPOSITIONS FOR SLEEPING DISORDERS

(75) Inventors: Hsiao Chang Chan, Hong Kong (HK);
Yu Lin Gou, Hong Kong (HK); Dewi Kenneth Rowlands, Hong Kong (HK);
Yiu Wa Chung, Hong Kong (HK)

(73) Assignee: Bright Future Pharmaceutical Laboratories, Hong Kong (HK)

( * ) Notice: Subject to any disclaimer, the term of this patent is extended or adjusted under 35 U.S.C. 154(b) by 1187 days.

(21) Appl. No.: 11/129,628

(22) Filed: May 13, 2005

(65) Prior Publication Data

US 2005/0261167 A1 Nov. 24, 2005

Related U.S. Application Data

(60) Provisional application No. 60/572,528, filed on May 18, 2004.

(51) Int. Cl.
| | |
|---|---|
| A01N 43/42 | (2006.01) |
| A01N 43/40 | (2006.01) |
| A01N 43/16 | (2006.01) |
| A61K 31/47 | (2006.01) |
| A61K 31/445 | (2006.01) |
| A61K 31/35 | (2006.01) |

(52) U.S. Cl. ............... 514/312; 514/320; 514/456
(58) Field of Classification Search ............... 514/312, 514/320, 456
See application file for complete search history.

(56) References Cited

U.S. PATENT DOCUMENTS

| 4,522,811 | A |   | 6/1985 | Eppstein et al. |
|---|---|---|---|---|
| 5,502,047 | A |   | 3/1996 | Kavey |
| 5,643,897 | A |   | 7/1997 | Kavey |
| 5,650,433 | A | * | 7/1997 | Watanabe et al. ............ 514/456 |
| 6,211,229 | B1 |   | 4/2001 | Kavey |
| 6,224,872 | B1 | * | 5/2001 | Shibuya et al. ............... 424/729 |
| 6,344,487 | B1 |   | 2/2002 | Kavey |
| 2003/0206895 | A1 | * | 11/2003 | Cavazza ........................ 424/94.1 |
| 2005/0272812 | A1 | * | 12/2005 | Pettegrew et al. ............ 514/546 |

FOREIGN PATENT DOCUMENTS

| WO | WO 01/26666 | 4/2001 |
|---|---|---|
| WO | WO 02/15901 | 2/2002 |

OTHER PUBLICATIONS

Jungluth et al. Fresenius J. Anal. Chem. 2000. vol. 367, pp. 661-666.*
International Search Report for PCT/US2005/016783, mailed Dec. 18, 2006, 19 pgs.
Bioadhesion—Possibilities and Future Trends; ed. by Gurny and Junginger. Stuttgart: Wiss. Verl.-Ges. (1990).
Carlson, Design and Optimization in Organic Synthesis, Elsevier Science Publishers, B.V. (1992).
Matsuda, Structural Requirements of Flavonoids and Related Compounds for Aldose Reductase Inhibitory Activity, Chemical & Pharmaceutical Bulletin, vol. 50, No. 6, pp. 788-795 (2002).
Cozanni et al., Efficient Photosensitization of Malignant Human Cells in Vitro by Liposome-Bound Porphyrins, Chem.-Biol. Interactions, vol. 53, pp. 131-143 (1985).
Jori et al., Preferential delivery of liposome-incorporated porphyrins to neoplastic cells in tumour-bearing rats, Br. J. Cancer, vol. 48, pp. 307-309 (1983).
Jori et al., Controlled targeting of different subcellular sites by porphyrins in tumour-bearing mice, Br. J. Cancer, vol. 53, No. 5, pp. 615-621 (1986).
Hosny et al., Hydroxylations and Methylations of Quercetin, Fisetin, and Catechin by Streptomyces griseus, Journal of Natural Products, vol. 64, No. 4, pp. 462-465 (2001).
Ikramov et al., Flavonoids of Lagonychium Farctum, Chemistry of Natural Compounds, vol. 26, No. 2, pp. 226-227 (1990), translated from Khimiya Prirodnykh Soedinenii, No. 2, pp. 274-276 (1990).
Jungbluth et al., Oxidation of flavonols with Cu(II) and Fe(II) and Fe(III) in aqueous media, J. Chem. Soc. Perkin Trans. vol. 2, pp. 1946-1952 (2000).
Sicuro et al., Dark- and Light-Interaction of Porphyrins with Malignant Cell Compartment, Med. Biol. Environ., vol. 15 pp. 67-70 (1987).
Smit et al., Organic Synthesis, The Science Behind the Art, The Royal Society of Chemistry (1998).
Zhiwu Xuebao, Studies on the Chemical Constituents of Limonium Aureum (L.) Hill, (English abstract) vol. 31, No. 3, pp. 205-208 (1989).
Bell et al., "Skeletal Advancement for the treatment of obstructive sleep apnea in children", Cleft Palate-Carniofacial Journal, vol. 38, No. 2, pp. 147-154 (2001).
Ford et al., "Epidemiologic study of sleep disturbance and psychiatric disorders", JAMA 262, pp. 1479-1484 (1989).
Kupfer et al., "Management of Insomnia", The New England J. of Med. vol. 336, No. 5, pp. 341-346 (1997).
Simon et al., "Prevalence, burden and treatment of insomnia in primary care", Am. J. Psychiatry 154, pp. 1417-1423 (1997).
Stafford et al., "Comparison of Proanthocyanidins and related compounds in leaves and leaf-derived cell cultures of Ginkgo bioloba L. Pseudotsuga menziesii Franco, and Ribes sanguineum Pursh", Plant Physiol. vol. 82, pp. 1132-1138 (1996).

* cited by examiner

Primary Examiner — Sreeni Padmanabhan
Assistant Examiner — Samira Jean-Louis
(74) Attorney, Agent, or Firm — Squire, Sanders & Dempsey (US) LLP

(57) ABSTRACT

Provided herein is a composition that contains an effective amount of one or more compounds for treating, preventing, or ameliorating a disorder such as insomnia or another sleeping disorder and using the composition.

7 Claims, 4 Drawing Sheets

NOTE: first stage is,biotransformation,methylation by streptomyces griseus,
Reactants: 2, Reagents: 1, Solvents: 2,
Steps: 1, Stages: 3

NOTE: Reactants: 1,
Steps: 1, Stages: 1

NOTE: Reactants: 2, Reagents: 1, Solvents: 1,
Steps: 2, Stages: 2

NOTE: electrochem.,
    Reactants: 1, Reagents: 2, Solvents: 2,
    Steps: 1, Stages: 1

COMPOSITIONS FOR SLEEPING DISORDERS

CROSS-REFERENCE TO RELATED APPLICATIONS

This application claims the priority of U.S. provisional application No. 60/572,528 filed on May 18, 2004, the teachings of which are incorporated herein by reference.

BACKGROUND OF THE INVENTION

1. Field of the Invention

This invention generally relates to a composition for treating, preventing or ameliorating insomnia and other sleeping disorders.

2. Description of the Background

A large percentage of the adult population suffers from insomnia in some form at some time in their lives. This may vary from a single episode of one night's duration to chronic conditions. Transient insomnia is an insomnia that is present for one to several days, and is less than one week in duration. Short term insomnia is an insomnia of one to three weeks in duration. Chronic insomnia is typically accepted to involve episodes greater than three (3) weeks in duration. The insomnia may further involve onset insomnia (difficulty in falling asleep) and/or maintenance insomnia (difficulty in maintaining uninterrupted sleep). It is well known that the sleep deprivation resulting from such insomnia adversely affects cognition, safety and quality of life.

Known treatments for insomnia include the administration of medication, either of the non-barbiturate or barbiturate type, shortly before bedtime. While both types of sedatives may be used to effectively treat insomnia, neither is without its undesirable side effects. Barbiturate type sedatives, such as secobarbital (sold by Eli Lilly and Company under the trade name of Seconal®) are general depressants. While effective, these medications are well known to lose their effectiveness after a few days. Furthermore, they are highly addictive and commonly abused.

The groups of medications now most commonly used for the treatment of insomnia are the imidazopyridines, the pyrazolopyrimidines and the benzodiazepines. There is one available hypnotic in the imidazopyridine group, one in the pyrazolopyrimidine group and there are five in the benzodiazepine group. They differ significantly in half lives but are otherwise very similar and equally effective. They have supplanted the barbiturates as the principal treatment for insomnia because they have less addiction potential and are associated with less risk for suicide than the barbiturates unless taken with alcohol. However, these groups, too, are addictive and their wide usage draws concern as their potential side effects become more apparent. These side effects include daytime sedation, decreased cognitive abilities such as memory loss and, most recently in the case of Halcion® (triazolam) and possibly Ambien® (zolpidem) and Sonata® (zaleplon), feelings of agitation after the drug's therapeutic effects pass.

Other pharmaceutical formulations, e.g., those described in U.S. Pat. Nos. 5,502,047, 5,643,897, 6,211,229, and 6,344,487 can be used for treating insomnia with limited effectiveness.

Therefore, there is a need for new compositions effective for treating insomnia and related disorders.

The compositions and embodiments thereof described herein address the above described problems and other needs.

SUMMARY OF THE INVENTION

Provided herein is a composition for treating, preventing or ameliorating insomnia and related disorders. The composition can include an effective amount of myricitrin, a related compound, or a pharmaceutically acceptable salt thereof. The composition may also include a physiologically acceptable carrier such as a pharmaceutically acceptable carrier. The composition can be formulated into any formulation for a desired mode of administration. The composition can be used to treat a disorder such as insomnia, depression-related disease, stress-related disease, depression-related sleep disorder, neurodegeneration diseases, Alzheimer's disease, Pick's disease, spinocerebellar degeneration, Parkinson's disease, chorea, glaucoma, amyotrophic lateral sclerosis, senile macular degeneration, hepatic encephalopathy, demyelinating diseases, Lewy body dementia, multi-infarct dementia, multiple sclerosis or combinations thereof.

DETAILED DESCRIPTION

Compositions Including Myricitrin or Related Compounds

Figure 1A:
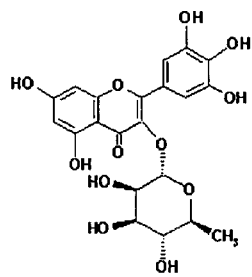
FIG. 1A shows the structure of myricitrin.

Provided herein is a composition for treating, preventing or ameliorating insomnia and related disorders. The composition can include an effective amount of myricitrin (FIG. 1A), a related compound, or a pharmaceutically acceptable salt thereof. The composition may also include a physiologically acceptable carrier such as a pharmaceutically acceptable carrier. The composition can be formulated into any formulation for a desired mode of administration.

Myricitrin and Related Compounds

In one embodiment, the composition includes an effective amount a compound of formulae I or II:

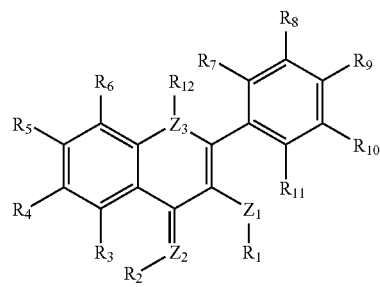

Formula I

Formula II

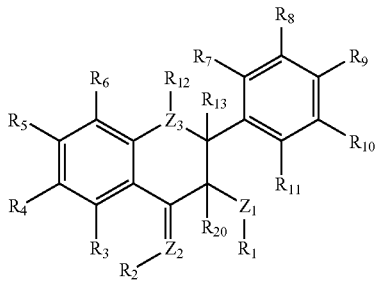

in which $R_1$-$R_{13}$, $R_{20}$ and $Z_1$-$Z_3$ substituents are defined as follows:

$R_1$, $R_2$, and $R_{12}$ taken independently can be, for example, absence, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule;

$R_3$, $R_4$, $R_5$, $R_6$, $R_7$, $R_8$, $R_9$, $R_{10}$, $R_{11}$, $R_{13}$ and $R_{20}$ taken independently can be, for example, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule;

$Z_1$, $Z_2$ and $Z_3$ taken independently can be, for example, oxygen (O), sulphur (S), or NH;

$Z_1$ and $R_1$ taken together can be, for example, a moiety of formula III:

Formula III

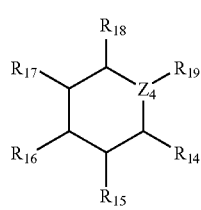

in which $R_{14}$, $R_{15}$, $R_{16}$, $R_{17}$, $R_{18}$ and $R_{19}$ taken independently can be for example, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule; and $Z_4$ can be oxygen (O), sulphur (S), or NH.

In some embodiments, any of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $Z_1$, $Z_2$, $Z_3$ and $Z_4$ of Formula I or II can exclude any of the groups provided herein. For example, $R_1$, $R_2$, $R_3$, $R_4$, $R_5$, $R_6$, $R_7$, $R_8$, $R_9$, $R_{10}$, $R_{11}$, $R_{12}$, $R_{14}$, $R_{15}$, $R_{16}$, $R_{17}$, $R_{18}$, $R_{19}$, $Z_1$, $Z_2$, $Z_3$ and $Z_4$ of Formula I taken together do not form myricetin (FIG. 1B) or any of the compounds listed in WO0215901. Myricetin is also known as 3,3'4'5,5',7-hexOH-Flavone, Cannabiscetin, myricetol, myricitin, or 3,3',4',5,5',7-Hexahydroxyflavone.

Figure 1B:
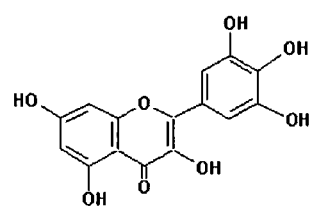
FIG. 1B shows the structure of myricetin.
Figure 2:
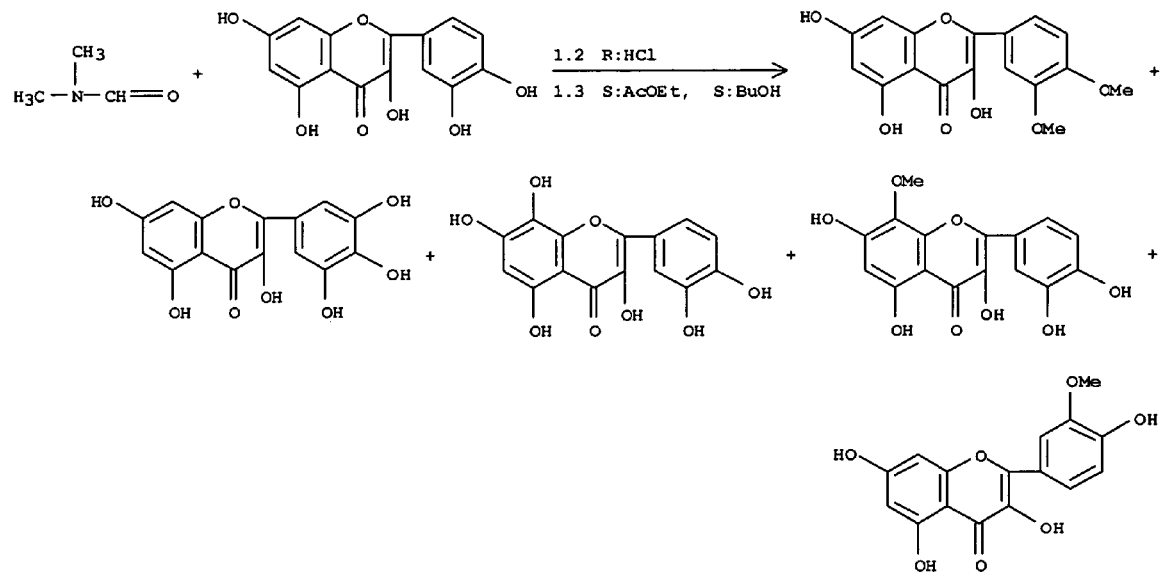
FIG. 2 shows a method of hydroxylation and methylation of a compound of Formula I.
Figure 3:
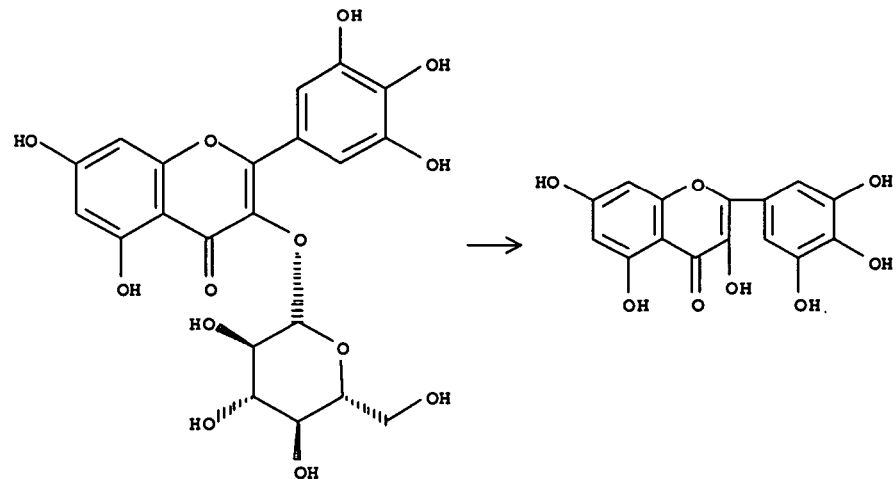
FIG. 3 shows a method of inter-transformation of a compound of Formula I to another compound as defined in Formula I.
Figure 4:
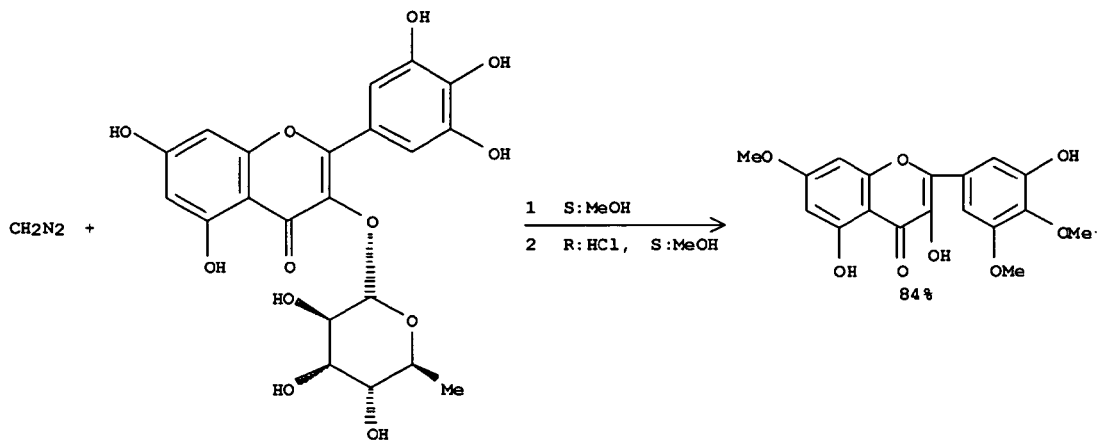
FIG. 4 shows a further method of inter-transformation of a compound of Formula I to another compound as defined in Formula I.
Figure 5:
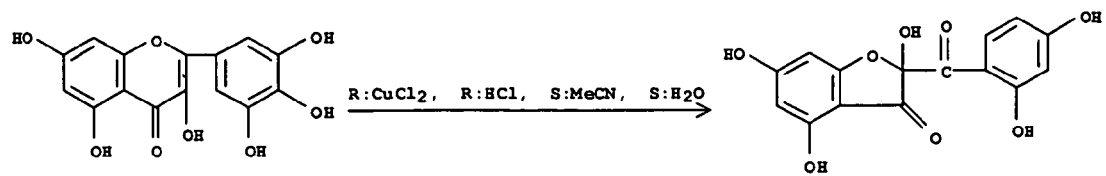
FIG. 5 shows a further method of inter-transformation of a compound of Formula I to a compound of Formula III.

In one embodiment, the compound of Formula I can be myricitrin (FIG. 1A). Myricitrin is also known as myricetol 3-rhamnoside, myricitrine, myricitroside, myricetrin, or 5,7-Dihydroxy-3-((2S,3R,4R,5R,6S)-3,4,5-trihydroxy-6-methyl-tetrahydro-pyran-2-yloxy)-2-(3,4,5-trihydroxy-phenyl)-1-benzopyran-4-one) and has a structure similar to that of myricetin (FIG. 1B).

The compound of formula II can be in a racemic form, a mixture of diastero isomers, or an enantiomer. The various enantiomers of the compound of formula II are shown in formulae IIa, IIb, IIc and IId:

Formula IIa

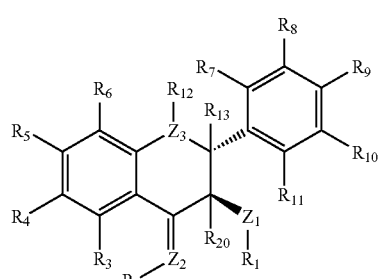

Formula IIb

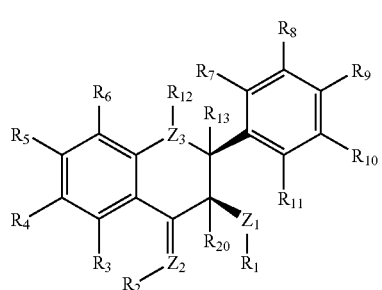

-continued

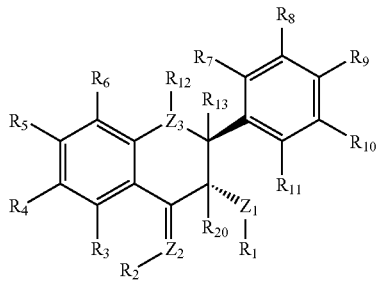

Formula IIc

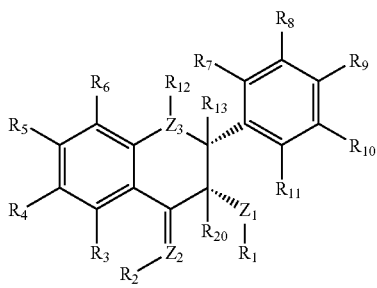

Formula IId in which $R_1$-$R_{13}$, $R_{20}$ and $Z_1$-$Z_3$ substituents are defined above.

In one embodiment, the compound of formula II can be a compound of formula IIe:

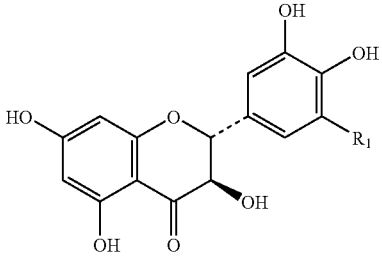

Formula IIe in which $R_1$ can be, for example, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule.

In another embodiment, the composition described herein can be a myricitrin derivative of Formula IV:

Formula IV in which $R_1$-$R_{13}$ and $Z_1$-$Z_3$ substituents are defined as follows:

$R_1$, $R_6$, and $R_8$ taken independently can be, for example, absence, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule;

$R_2$, $R_3$, $R_4$, $R_5$, $R_7$, $R_9$, $R_{10}$, $R_{11}$, $R_{12}$ and $R_{13}$ taken independently can be, for example, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule;

$Z_1$, $Z_2$ and $Z_3$ taken independently can be, for example, oxygen (O), sulphur (S), or NH; and $Z_1$ and $R_1$ taken together can be, for example, a moiety of formula III:

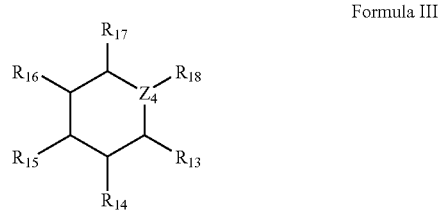

Formula III in which $R_{13}$, $R_{14}$, $R_{15}$, $R_{16}$, $R_{17}$, and $R_{18}$ taken independently can be for example, hydrogen, halo, alkyl, substituted alkyl, alkoxy, cycloalkyl, heterocyclic, alkenyl alkyl, alkenyl, substituted alkenyl, alkynyl, substituted alkynyl, phenyl, substituted phenyl, aryl, substituted aryl, heteroaryl, substituted heteroaryl, hydroxyl, alkoxy, substituted alkoxy, phenoxy, substituted phenoxy, aroxy, substituted aroxy, thiol, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, fulfonyl, substituted sulfonyl, polyaryl, substituted polyaryl, C1-C20 cyclic, substituted C1-C20 cyclic, heterocyclic, substituted heterocyclic, amino acid, peptide, polyether, polyester, polypeptide, protein, polyphosphazene, polyalkylene oxide, polyalkylene glycol, polyethylene glycol, polyalkylene, a bioactive agent, or a drug molecule.

In some embodiments, any of $R_1$, $R_2$, $R_3$, $R_4$, $R_5$, $R_6$, $R_7$, $R_8$, $R_9$, $R_{10}$, $R_{11}$, $R_{12}$, $R_{13}$, $Z_1$, $Z_2$ and $Z_3$ of Formula IV can exclude any of the groups provided herein. For example, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $Z_1$, $Z_2$, $Z_3$ and $Z_4$ of Formula IV taken together do not form any of the myricetin derivative as shown in FIG. 1B.

Some other representative myricitrin derivatives are listed in Table 1.

TABLE 1

Some exemplary structures of myricitrin derivatives

Structure

1

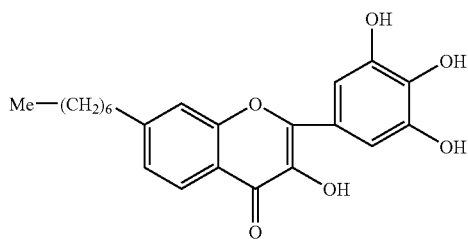

Formula: C22 H24 O6
CA Index Name: 4H-1-Benzopyran-4-one, 7-heptyl-3-hydroxy-2-(3,4,5-trihydroxyphenyl)-(9CI)

2

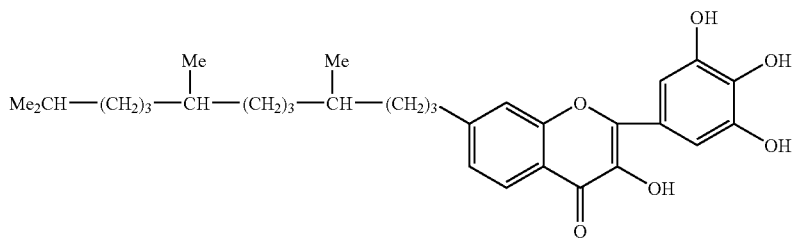

Formula: C31H42 O6
CA Index Name: 4H-1-Benzopyran-4-one, 3-hydroxy-2-(3,4,5-trihydroxyphenyl)-7-(4,8,12-trimethyltridecyl)-(9CI)

3

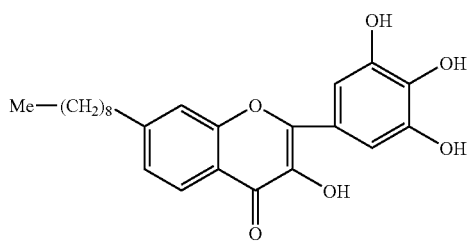

Formula: C24 H28 O6
CA Index Name: 4H-1-Benzopyran-4-one, 3-hydroxy-7-nonyl-2-(3,4,5-trihydroxyphenyl)-(9CI)

TABLE 1-continued

Some exemplary structures of myricitrin derivatives

Structure

4
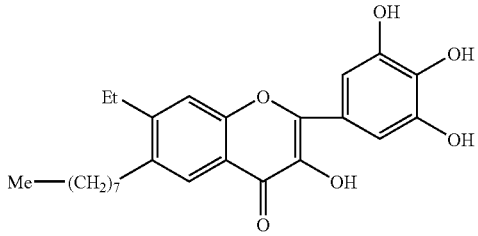

Formula: C25 H30 O6
CA Index Name: 4H-1-Benzopyran-4-one, 7-ethyl-3-hydroxy-6-octyl-2-(3,4,5-trihydroxyphenyl)-(9Cl)

5
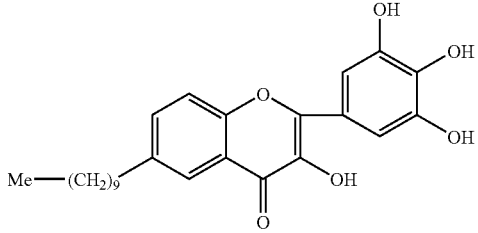

Formula: C25 H30 O6
CA Index Name: 4H-1-Benzopyran-4-one, 6-decyl-3-hydroxy-2-(3,4,5-trihydroxyphenyl)-(9Cl)

6
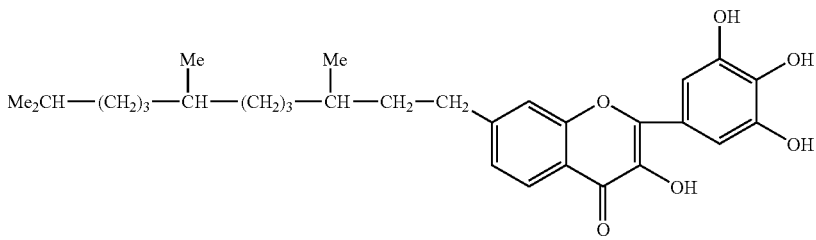

Formula: C30 H40 O6
CA Index Name: 4H-1-Benzopyran-4-one, 3-hydroxy-2-(3,4,5-trihydroxyphenyl)-7-(3,7,11-trimethyldodecyl)-(9Cl)

7
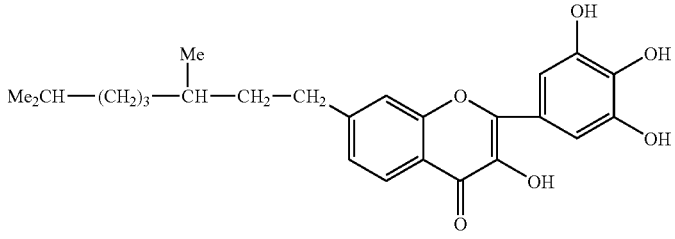

Formula: C25 H30 O6
CA Index Name: 4H-1-Benzopyran-4-one, 7-(3,7-dimethyloctyl)-3-hydroxy-2-(3,4,5-trihydroxyphenyl)-(9Cl)

TABLE 1-continued

Some exemplary structures of myricitrin derivatives

Structure

8 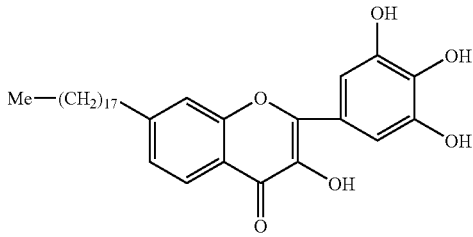

Formula: C33 H46 O6
CA Index Name: 4H-1-Benzopyran-4-one, 3-hydroxy-7-octadecyl-2-(3,4,5-trihydroxyphenyl)-(9Cl)

9 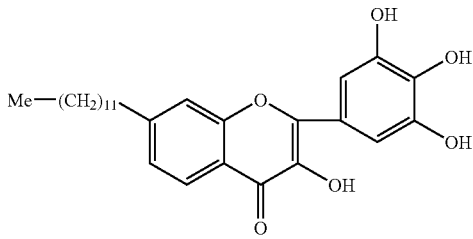

Formula: C27 H34 O6
CA Index Name: 4H-1-Benzopyran-4-one, 7-dodecyl-3-hydroxy-2-(3,4,5-trihydroxyphenyl)-(9Cl)

10 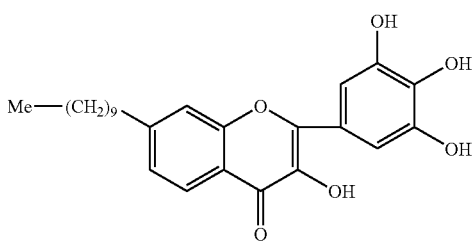

Formula: C25 H30 O6
CA Index Name: 4H-1-Benzopyran-4-one, 7-decyl-3-hydroxy-2-(3,4,5-trihydroxyphenyl)-(9Cl)

11 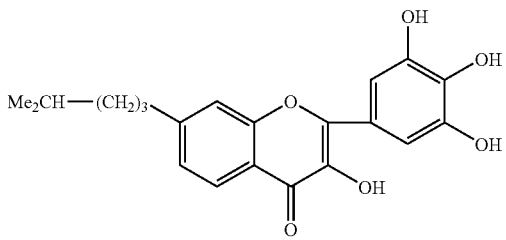

Formula: C21 H22 O6
CA Index Name: 4H-1-Benzopyran-4-one, 3-hydroxy-7-(4-methylpentyl)-2-(3,4,5-trihydroxyphenyl)-(9Cl)

TABLE 1-continued

Some exemplary structures of myricitrin derivatives

Structure

12

Formula: C23 H26 O6
CA Index Name: 4H-1-Benzopyran-4-one, 3-hydroxy-7-octyl-2-(3,4,5-trihydroxyphenyl)-(9Cl)

13

Formula: C21 H22 O6
CA Index Name: 4H-1-Benzopyran-4-one, 7-hexyl-3-hydroxy-2-(3,4,5-trihydroxyphenyl)-(9Cl)

14

Formula: C19 H18 O6
CA Index Name: 4H-1-Benzopyran-4-one, 7-butyl-3-hydroxy-2-(3,4,5-trihydroxyphenyl)-(9Cl)

15

Formula: C17 H14 O6
CA Index Name: 4H-1-Benzopyran-4-one, 7-ethyl-3-hydroxy-2-(3,4,5-trihydroxyphenyl)-(9Cl)

TABLE 1-continued

Some exemplary structures of myricitrin derivatives

Structure

16

Formula: C16 H12 O9
CA Index Name: 4H-1-Benzopyran-4-one, 3,5-dihydroxy-7-
methoxy-2-(2,3,4,5-tetrahydroxyphenyl)-(9Cl)

17

Formula: C15 H10 O10
CA Index Name: 4H-1-Benzopyran-4-one, 3,5,7-
trihydroxy-2-(pentahydroxyphenyl)-(9Cl)

18

Formula: C15 H10 C9
CA Index Name: 4H-1-Benzopyran-4-one, 3,5,7-trihydroxy-2-
(2,3,4,5-tetrahydroxyphenyl)-(9Cl)

19

Absolute stereochemistry. Rotation (−)
Formula: C27 H30 O17
CA Index Name: 4H-1-Benzopyran-4-one, 7-[[6-O-(6-
deoxy-α-L-mannopyranosyl)-β-D-glucopyranosyl]oxy]-
3,5-dihydroxy-2-(3,4,5-trihydroxyphenyl)-(9Cl)

TABLE 1-continued

Some exemplary structures of myricitrin derivatives

Structure

20

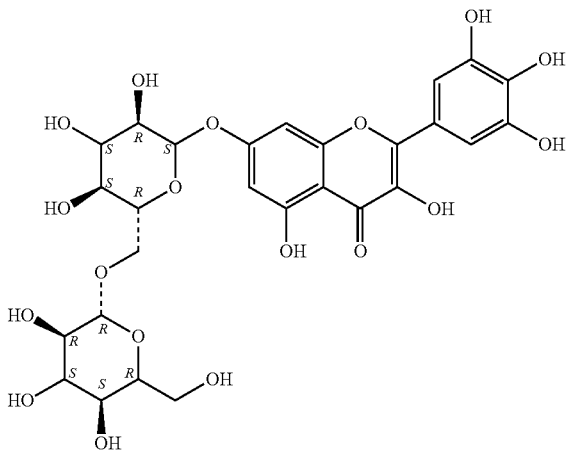

Absolute stereochemistry. Rotation (−)
Formula: C27 H30 O18
CA Index Name: 4H-1-Benzopyran-4-one, 7-[(6-O-β-D-glucopyranosyl-β-D-glucopyranosyl)oxy]-3,5-dihydroxy-2-(3,4,5-trihydroxyphenyl)-(9Cl)

21

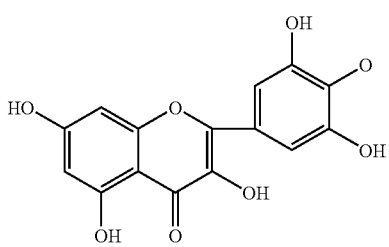

Formula: C15 H9 O8
CA Index Name: Phenoxy, 2,6-dihydroxy-4-(3,5,7-trihydroxy-4-oxo-4H-1-benzopyran-2-yl)-(9Cl)

22

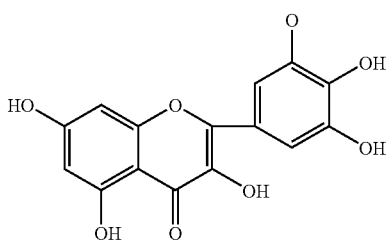

Formula: C15 H9 O8
CA Index Name: Phenoxy, 2,3-dihydroxy-5-(3,5,7-trihydroxy-4-oxo-4H-1-benzopyran-2-yl)-(9Cl)

23

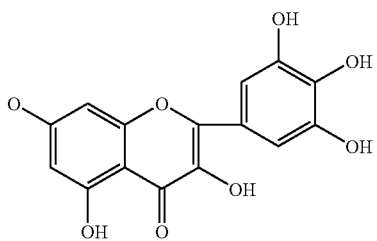

Formula: C15 H9 O8
CA Index Name: Phenoxy, 2,3-dihydroxy-5-(3,5,7-trihydroxy-4-oxo-4H-1-benzopyran-2-yl)-(9Cl)

TABLE 1-continued

Some exemplary structures of myricitrin derivatives

Structure

24 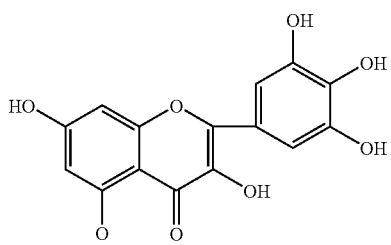

Formula: C15 H9 O8
CA Index Name: 4H-1-Benzopyran-7-yloxy, 3,5-dihydroxy-4-oxo-2-(3,4,5-trihydroxyphenyl)-(9Cl)

25 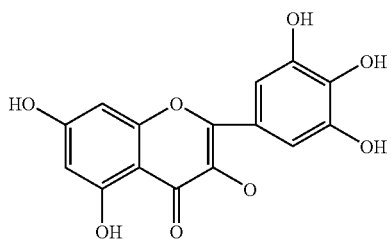

Formula: C15 H9 O8
CA Index Name: 4H-1-Benzopyran-5-yloxy, 3,7-dihydroxy-4-oxo-2-(3,4,5-trihydroxyphenyl)-(9Cl)

26 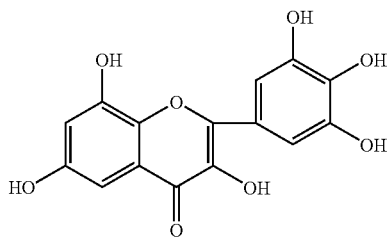

Formula: C15 H9 O8
CA Index Name: 4H-1-Benzopyran-3-yloxy, 5,7-dihydroxy-4-oxo-2-(3,4,5-trihydroxyphenyl)-(9Cl)

27 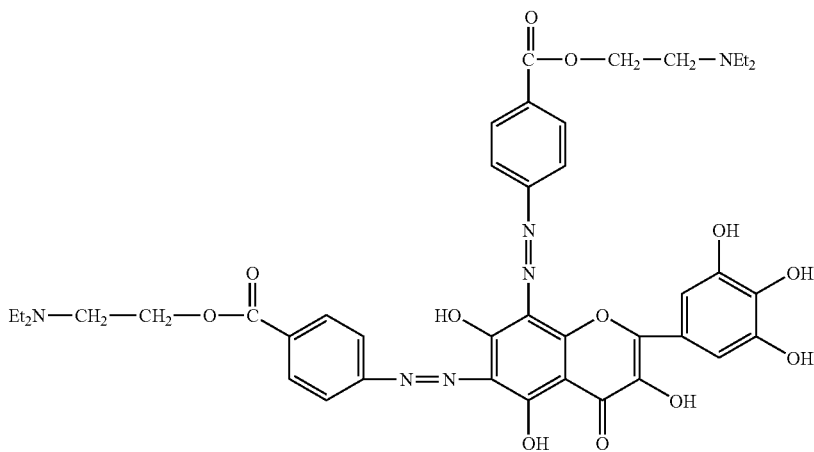

Formula: C15 H10 O8
CA Index Name: 4H-1-Benzopyran-4-one, 3,6,8-trihydroxy-2-(3,4,5-trihydroxyphenyl)-(9Cl)

TABLE 1-continued
Some exemplary structures of myricitrin derivatives
Structure
28
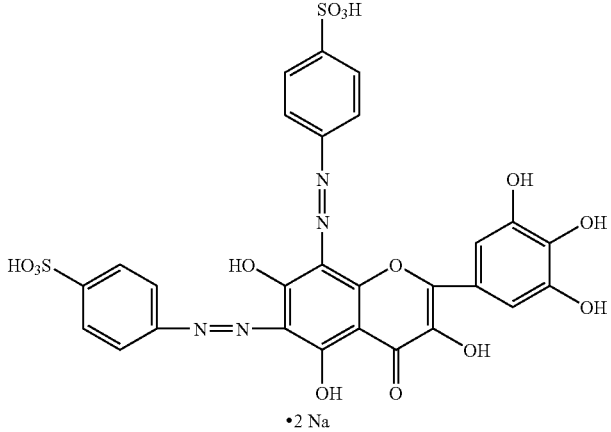
Formula: C41 H44 N6 O12
CA Index Name: Benzoic acid, 4,4'-[[3,5,7-trihydroxy-4-oxo-2-
(3,4,5-trihydroxyphenyl)-4H-1-benzopyran-6,8-diyl]bis(azo)]bis-,
bis[2-(diethylamino)ethyl] ester(9Cl)
29
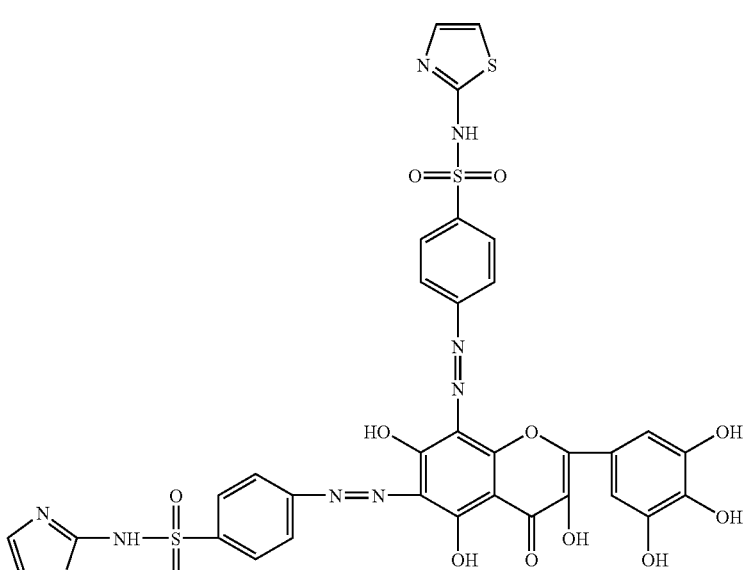
Formula: C27 H18 N4 O14 S2.2 Na
CA Index Name: Benzenesulfonic acid, 4,4'-4[[3,5,7-
trihydroxy-4-oxo-2-(3,4,5-trihydroxyphenyl)-4H-1-
benzopyran-6,8-diyl]bis(azo)]bis-, disodium salt (9Cl)

TABLE 1-continued
Some exemplary structures of myricitrin derivatives
Structure
30
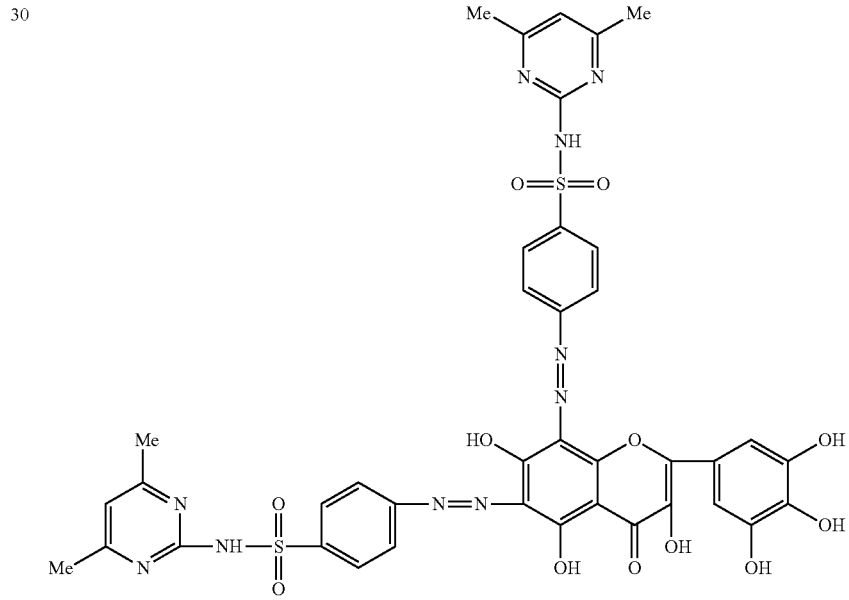
Formula: C33 H22 N8 O12 S4
CA Index Name: Benzenesulfonamide, 4,4'-[[3,5,7-trihydroxy-4-oxo-2-(3,4,5-trihydroxyphenyl)-4H-1-benzopyran-6,8-diyl]bis(azo)]bis[N-2-thiazolyl-(9CI)
31
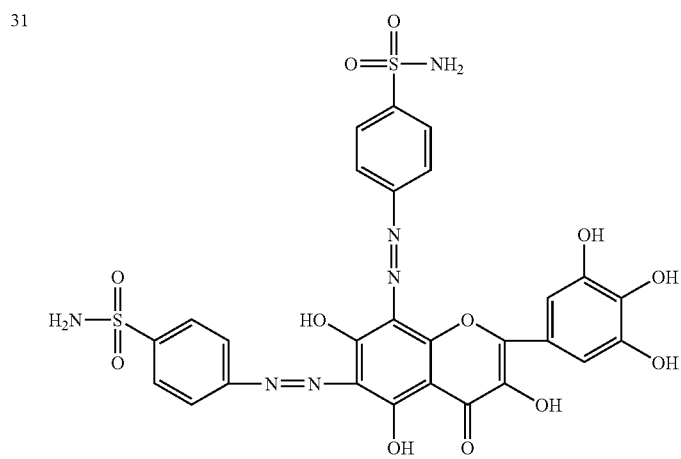
Formula: C39 H32 N10 O12 S2
CA Index Name: Benzenesulfonamide, 4,4'[[3,5,7-trihydroxy-4-oxo-2-(3,4,5-trihydroxyphenyl)-4H-1-benzopyran-6,8-diyl]bis(azo)]bis[N-(4,6-dimethyl-2-pyrimidinyl)-(9CI)

TABLE 1-continued

Some exemplary structures of myricitrin derivatives

Structure

32

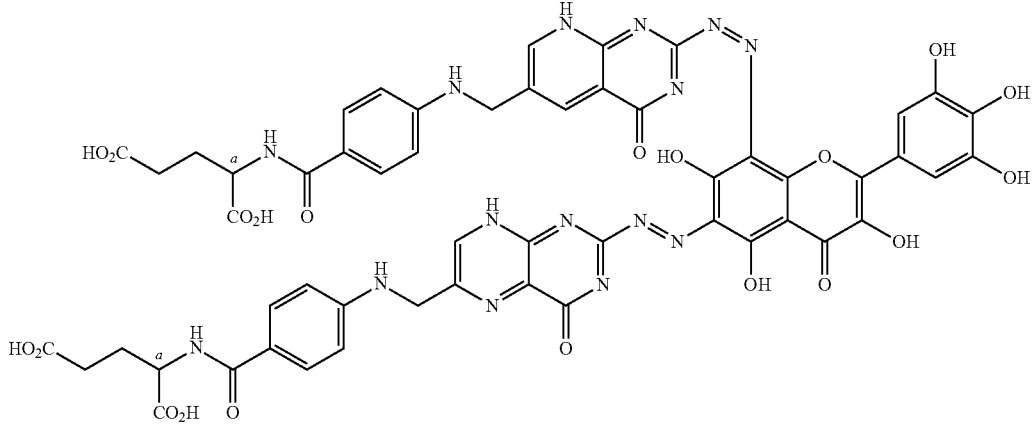

Absolute stereochemistry. Double bond geometry unknown
Formula: C27 H20 N6 O12 S2
CA Index Name: Benzenesulfonamide, 4,4-[[3,5,7-trihydroxy-4-oxo-2-(3,4,5-trihydroxyphenyl)-4H-1-benzopyran-6,8-diyl]bis(azo)]bis-(9Cl)

33

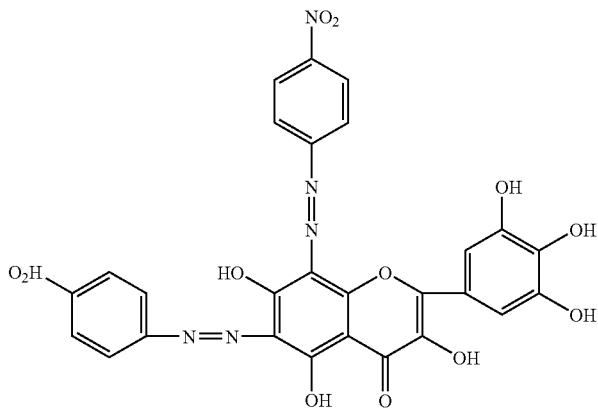

Formula: C27 H16 N6 O12
CA Index Name: 4H-1-Benzopyran-4-one, 3,5,7-trihydroxy-6,8-bis[(4-nitrophenyl)azo]-2-(3,4,5-trihydroxyphenyl)-(9Cl)

34

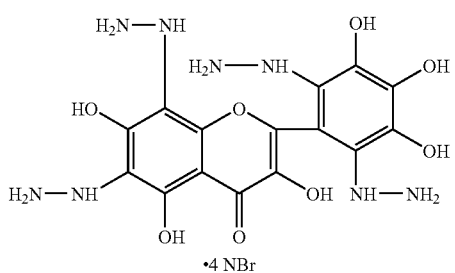

Formula: C15 H18 N8 O8.4 Br H
CA Index Name: 4H-1-Benzopyran-4-one, 2-(2,6-dihydrazino-3,4,5-trihydroxyphenyl)-6,8-dihydrazino-3,5,7-trihydroxy-, tetrahydrobromide (9Cl)

TABLE 1-continued

Some exemplary structures of myricitrin derivatives

Structure

35 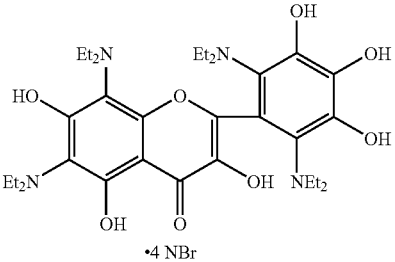

Formula: C31 H46 N4 O8.4 Br H
CA Index Name: 4H-1-Benzopyran-4-one, 2-[2,6-bis(diethylamino)-3,4,5-trihydroxyphenyl]-6,8-bis(diethylamino)-3,5,7-trihydroxy-, tetrahydrobromide (9Cl)

36 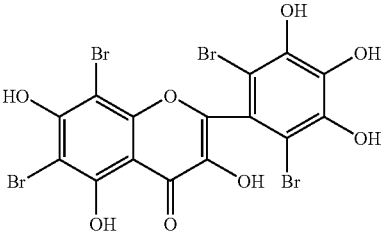

Formula: C15 H6 Br4 O8
CA Index Name: 4H-1-Benzopyran-4-one, 6,8-dibromo-2-(2,6-dibromo-3,4,5-trihydroxyphenyl)-3,5,7-trihydroxy-(9Cl)
Other Names: 2',6,6',8-Tetrabromomyrcetin 37 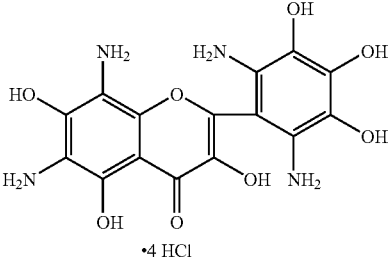

Formula: C15 H14 N4 O8.4 Cl H
CA Index Name: 4H-1-Benzopyran-4-one, 6,8-diamino-2-(2,6-diamino-3,4,5-trihydroxyphenyl)-3,5,7-trihydroxy-, tetrahydrochloride (9Cl)
Other Names: 2',6,6',8-Tetraaminomyrcetin tetrahydrochloride 38 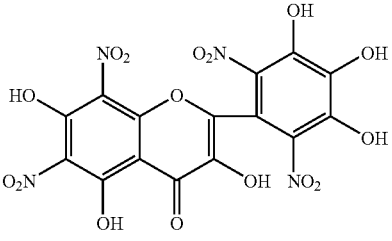

Formula: C15 H6 N4 O16
CA Index Name: 4H-1-Benzopyran-4-one, 3,5,7-trihydroxy-6,8-dinitro-2-(3,4,5-trihydroxy-2,6-dinitrophenyl)-(9Cl)
Other Names: 2',6,6',8-Tetranitromyrcetin TABLE 1-continued Some exemplary structures of myricitrin derivatives Structure

39

Absolute stereochemistry
Formula: C28 H24 O17
CA Index Name: 4H-1-Benzopyran-4-one, 3,5
dihydroxy-7-[[6-O-(3,4,5-trihydroxybenzoyl)-β-D-
glucopyranosyl]oxy]-2-(3,4,5-trihydroxyphenyl)-(9Cl)

40

| Component Registry | Component Registry |
|---|---|
| Number: 529-44-2 | Number: 492-62-6 |

Formula: C21 H20 O13
CA Index Name: 4H-1-Benzopyran-4-one, 3(5 or 7)-(α-D-
glucopyranosyloxy)-5,7(3,7 or 3,5)-dihydroxy-2-(3,4,5-
trihydroxyphenyl)-(9Cl)

41

Absolute stereochemistry
Formula: C21 H20 O12
CA Index Name: 4H-1-Benzopyran-4-one, 7-[(6-
deoxy-α-L-mannopyranosyl)oxy]-3,5-dihydroxy-2-
(3,4,5-trihydroxyphenyl)-(9Cl)

TABLE 1-continued

Some exemplary structures of myricitrin derivatives

Structure

42

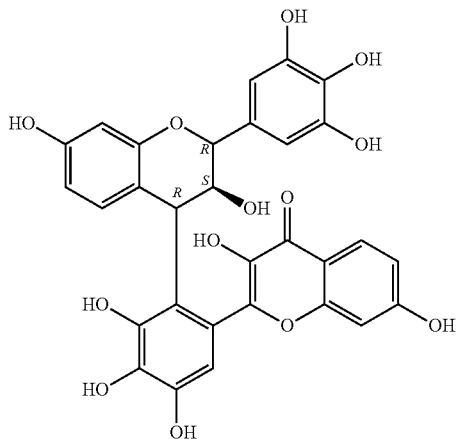

Absolute stereochemistry
Formula: C30 H22 O13
CA Index Name: 4H-1-Benzopyran-4-one, 2-[2-[3,4-dihydro-3,7-
dihydroxy-2-(3,4,5-trihydroxyphenyl)-2H-1-benzopyran-4-yl]-
3,4,5-trihydroxyphenyl]-3,7-dihydroxy-, [2R-(2α,3β,4α)]-(9CI)

43

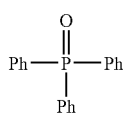 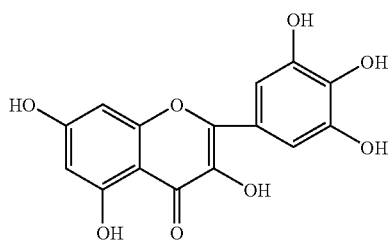

Component Registry  Component Registry
Number: 791-28-6  Number: 529-44-2
Formula: C18 H15 O P ½ C15 R10 O8
CA Index Name: 4H-1-Benzopyran-4-one, 3,5,7-
trihydroxy-2-(3,4,5-trihydroxyphenyl)-, compd. with
triphenylphosphine oxide (1:2) (9CI)
Other Names: Phosphine oxide, triphenyl-, compd.
with 3,5,7-trihydroxy-2-(3,4,5-trihydroxyphenyl)-4H-1-
benzopyran-4-one (2:1)(9CI); Myricetin
triphenylphosphine oxide complex (1:2)

44

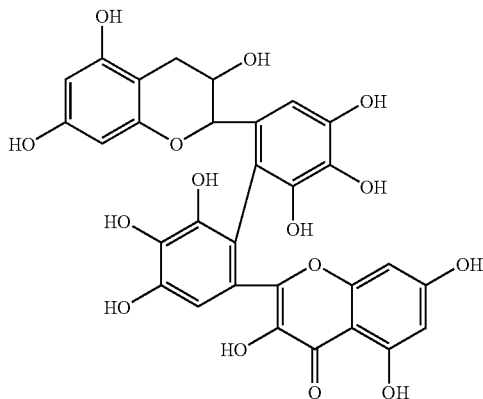

Formula: C30 H22 O15
CA Index Name: 4H-1-Benzopyran-4-one, 2-[6'-(3,4-dihydro-
3,5,7-trihydroxy-2H-1-benzopyran-2-yl)-2',3',4,4',5,6-
hexahydroxy[1,1'-biphenyl]-2-yl]-3,5,7-trihydroxy-, [2R-
[2α(R*),3α]]-(9CI)

TABLE 1-continued

Some exemplary structures of myricitrin derivatives

Structure

45

Component Registry Number: 529-44-2

Component Registry Number: 520-18-3

Component Registry Number: 117-39-5
Formula: C15 H10 O8.C15 H10 O7.C15 H10 O6
CA Index Name: 4H-1-Benzopyran-4-one, 2-(3,4-dihydroxyphenyl)-3,5,7-trihydroxy-, mixt. with 3,5,7-trihydroxy-2-(4-hydroxyphenyl)-4H-1-benzopyran-4-one and 3,5,7-trihydroxy-2-(3,4,5-trihydroxyphenyl)-4H-1-benzopyran-4-one(9CI)
Other Names: 4H-1-Benzopyran-4-one, 3,5,7-trihydroxy-2-(3,4,5-trihydroxyphenyl)-, mixt. contg. (9CI); 4H-1-Benzopyran-4-one, 3,5,7-trihydroxy-2-(4-hydroxyphenyl)-, mixt. contg. (9CI); Camellia ID 253

46

Formula: C15 H9 O8
CA Index Name: 4H-1-Benzopyran-4-one, 3,5,7-dihydroxy-2-(3,4,5-trihydroxyphenyl)-, ion(1-)(9CI)

47

Formula: C15 H10 O8.H
CA Index Name: 4H-1-Benzopyran-4-one, 3,5,7-trihydroxy-2-(3,4,5-trihydroxyphenyl)-, conjugate monoacid (9CI)

TABLE 1-continued

Some exemplary structures of myricitrin derivatives

Structure

48

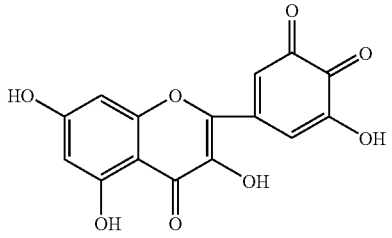

Formula: C15 H8 O8
CA Index Name: 3,5-Cyclohexadiene-1,2-dione, 3-hydroxy-5-
(3,5,7-trihydroxy-4-oxo-4H-1-benzopyran-2-yl)-(9Cl)

49

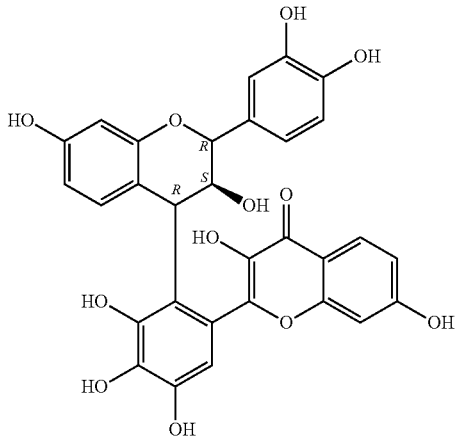

Absolute stereochemistry
Formula: C30 H22 O12
CA Index Name: 4H-1-Benzopyran-4-one, 2-[2-[2-(3,4-
dihydroxyphenyl)-3,4-dihydro-3,7-dihydroxy-2H-1-
benzopyran-4-yl]-3,4,5-trihydroxyphenyl]-3,7-
dihydroxy-, [2R-(2α,3β,4α)]-(9Cl)

50

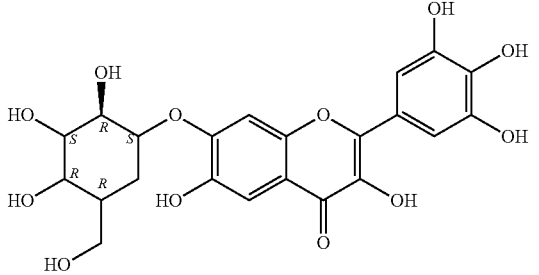

Absolute stereochemistry
Formula: C21 H20 O13
CA Index Name: 4H-1-Benzopyran-4-one, 7-(β-D-
galactopyranosyloxy)-3,6-dihydroxy-2-(3,4,5-trihydroxyphenyl)-
(9Cl)

TABLE 1-continued

Some exemplary structures of myricitrin derivatives

Structure

51

Absolute stereochemistry
Formula: C21 H20 O13
CA Index Name: 4H-1-Benzopyran-4-one, 7(β-D-galactopyranosyloxy)-3,5-dihydroxy-2-(3,4,5-trihydroxyphenyl)-(9Cl)

52

Formula: C20 H18 O12
CA Index Name: 4H-1-Benzopyran-4-one, 7-(arabinosyloxy)-3,5-dihydroxy-2-(3,4,5-trihydroxyphenyl)-(9Cl)

53

Formula: C15 H10 O8
CA Index Name: Flavone, 3,3',4',5',7,8-hexahydroxy-(6Cl)

54

Formula: C15 H10 O7
CA Index Name: 4H-1-Benzopyran-4-one, 3,5-dihydroxy-2-(3,4,5-trihydroxyphenyl)-(9Cl)
Other Names: Flavone, 3,3',4',5,5'-pentahydroxy-(6Cl)

TABLE 1-continued

Some exemplary structures of myricitrin derivatives

Structure

55 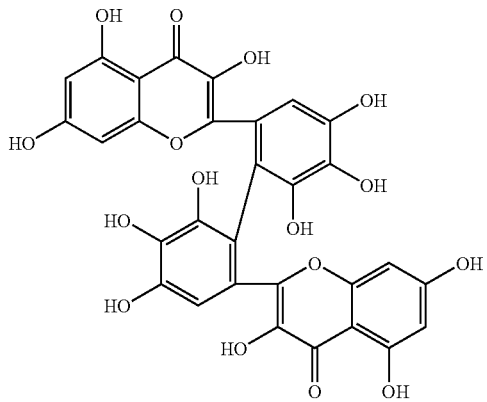

Formula: C30 H18 O16
CA Index Name: 4H-1-Benzopyran-4-one, 2,2'-(4,4',5,5',6,6'-hexahydroxy[1,1'-biphenyl]-2,2'-diyl)bis[3,5,7-trihydroxy-(9Cl)
Other Names: 2',2'''-Biflavone, 3,3',3'',3''',4',4''',5,5',5'',5''',7,7''-dodecahydroxy-(7Cl)

56 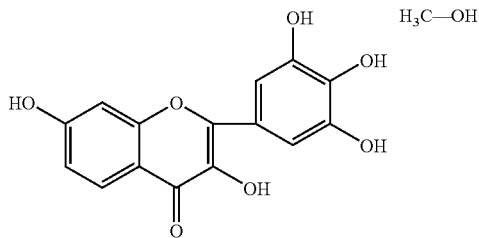

Component Registry Number: 490-31-3
Formula: C15 H10 O7.C H4 O
CA Index Name: Flavone, 3,3',4',5',7-pentahydroxy-, compd. with MeOH (7Cl)

Component Registry Number: 67-56-1

57 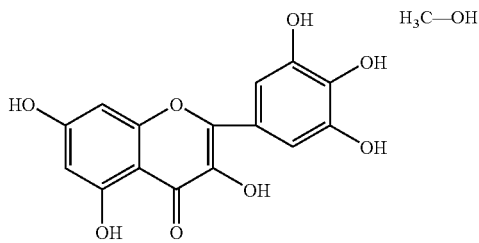

Component Registry Number: 529-44-2
Formula: C16 H12 O8
CA Index Name: Flavone, 3,3',4',5,5',7-hexahydroxy-, monomethyl ether (7Cl)

Component Registry Number: 67-56-1

TABLE 1-continued

Some exemplary structures of myricitrin derivatives

Structure

58 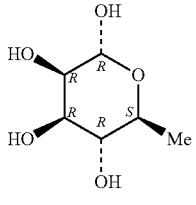

Absolute stereochemistry
Component Registry
Number: 6014-42-2
Formula: C21 H20 O12
CA Index Name: 4H-1-Benzopyran-4-one, 3,5,7-trihydroxy-2-(3,4,5-trihydroxyphenyl)-, mono(6-deoxy-a-L-mannopyranoside) (9CI)

Component Registry
Number: 529-44-2

59 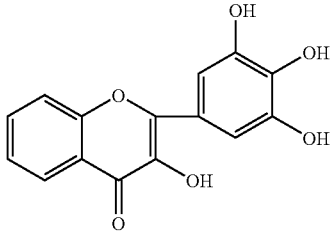

Formula: C15 H10 O6
CA Index Name: 4H-1-Benzopyran-4-one, 3-hydroxy-2-(3,4,5-trihydroxyphenyl)-(9CI)
Other Names: Flavone, 3,3',4',5'-tetrahydroxy-(7CI)

60 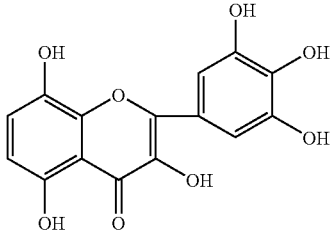

Formula C15 H10 O8
CA Index Name: 4H-1-Benzopyran-4-one, 3,5,8-trihydroxy-2-(3,4,5-trihydroxyphenyl)-(9CI)
Other Names: Flavone,3,3',4',5,5',8-hexahydroxy-(6CI); 3,5,8,3',4',5'-Hexahydroxyflavone 61 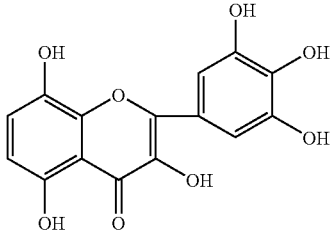

Absolute stereochemistry
Component Registry Number: 34069-06-2
Formula: C27 H30 O18
CA Index Name: 4H-1-Benzopyran-4-one, 7-[(O-β-D-glucopyranosyl-β-D-glucopyranosyl)oxy]-3,5-dihydroxy-2-(3,4,5-trihydroxyphenyl)-(9CI)

Absolute stereochemistry.
Rotation (+)
Component Registry Number: 492-61-5

TABLE 1-continued
Some exemplary structures of myricitrin derivatives
Structure
62
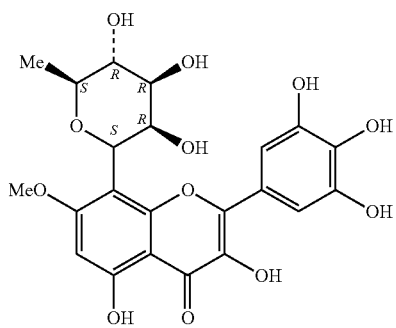
Formula: C22 H22 O12
CA Index Name: 4H-1-Benzopyran-4-one, 8-(6-deoxy-α-L-mannopyranosyl)-3,5-dihydroxy-7-methoxy-2-(3,4,5-trihydroxyphenyl)-(9Cl)
63
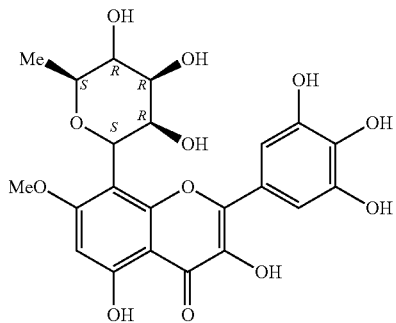
Formula: C15 H10 O8
CA Index Name: 4H-1-Benzopyran-4-one, 3,5,6-trihydroxy-2-(3,4,5-trihydroxyphenyl)-(9Cl)
64
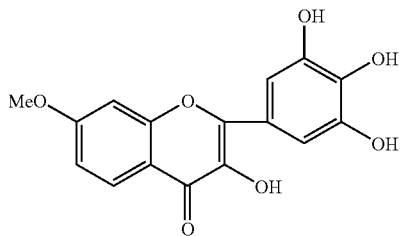
Formula: C16 H12 O7
CA Index Name: 4H-1-Benzopyran-4-one, 3-hydroxy-7-methoxy-2-(3,4,5-trihydroxyphenyl)-(9Cl)

TABLE 1-continued

Some exemplary structures of myricitrin derivatives

Structure

65 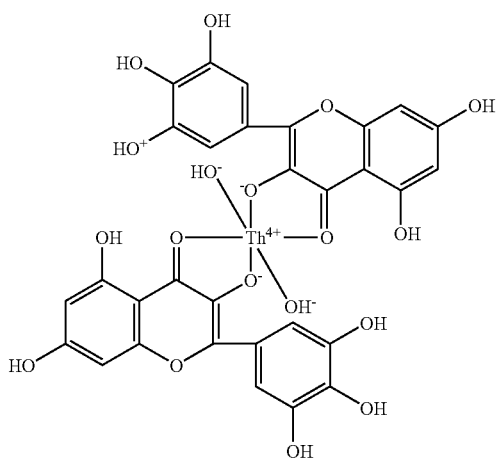

Formula: C30 H20 O18 Th
CA Index Name: Thorium, dihydroxybis[3,5,7-trihydroxy-2-(3,4,5-trihydroxyphenyl)-4H-1-benzopyran-4-onato-O3,O4]-(9CI)
Other Names: 4H-1-Benzopyran-4-one, 3,5,7-trihydroxy-2-(3,4,5-trihydroxyphenyl)-, thorium complex 66 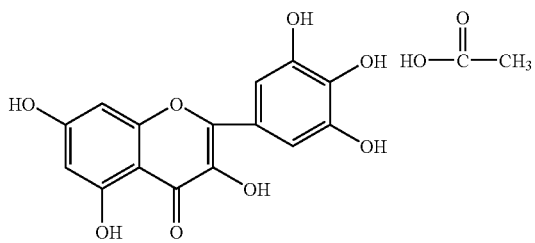

Component Registry Number: 529-44-2
Formula: C15 H10 O8.x C2 H4 O2
CA Index Name: 4H-1-Benzopyran-4-one, 3,5,7-trihydroxy-2-(3,4,5-trihydroxyphenyl)-, acetate(9CI)

Component Registry Number: 64-19-7

67 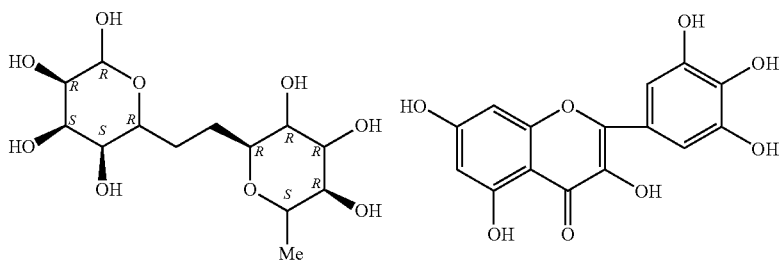

Component Registry Number: 26184-96-3
Formula: C27 H30 O17
CA Index Name: 4H-1-Benzopyran-4-one, 3,5,7-trihydroxy-2-(3,4,5-trihydroxyphenyl)-, mono[6-O-(6-deoxy-α-L-mannopyranosyl)-β-D-glucopyranoside] (9CI)

Component Registry Number: 529-44-2

TABLE 1-continued

Some exemplary structures of myricitrin derivatives

Structure

68
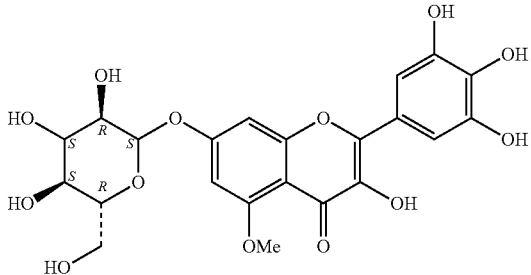

Absolute stereochemistry
Formula: C22 H22 O13
CA Index Name: 4H-1-Benzopyran-4-one, 7-(β-D-glucopyranosyloxy)-3-hydroxy-5-methoxy-2-(3,4,5-trihydroxyphenyl)-(9Cl)
Other Names: 5-Methoxymyricetin 7-O-glucoside 69
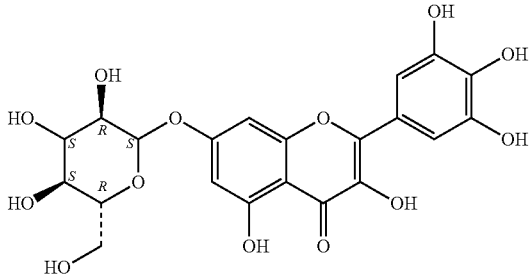

Absolute stereochemistry
Formula: C21 H20 O13
CA Index Name: 4H-1-Benzopyran-4-one, 7-(β-D-glucopyranosyloxy)-3,5-dihydroxy-2-(3,4,5-trihydroxyphenyl)-(9Cl)
Other Names: Flavone, 3,3',4',5,5',7-hexahydroxy-, 7-β-D-glucopyranoside (8Cl); Myricetin 7-β-D glucopyranoside; Myricetin 7-O-glucoside 70
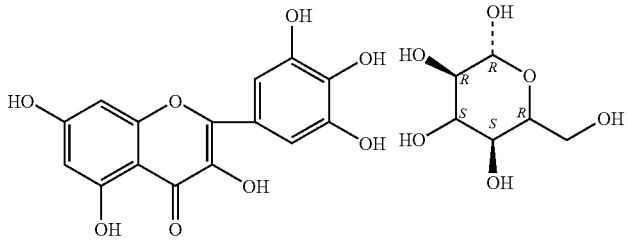

Component Registry Number: 529-44-2
Formula: C21 H20 O13
CA Index Name: 4H-1-Benzopyran-4-one, 3,5,7-trihydroxy-2-(3,4,5-trihydroxyphenyl)-, mono-β-D-glucopyranoside (9Cl)
Other Names: Flavone, 3,3',4',5,5',7-hexahydroxy-, glucoside (7Cl); Flavone, 3,3',4',5,5',7-hexahydroxy-, mono-β-D-glucopyranoside (8Cl); Myricetin glucoside Absolute stereochemistry. Rotation (+)
Component Registry Number: 492-61-5

TABLE 1-continued

Some exemplary structures of myricitrin derivatives

Structure

71 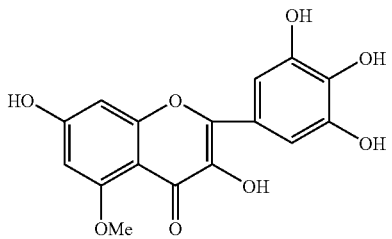

Formula: C16 H12 O8
CA Index Name: 4H-1-Benzopyran-4-one, 3,7-dihydroxy-5-methoxy-2-(3,4,5-trihydroxyphenyl)-(9Cl)
Other Names: Flavone, 3,3',4',5',7-pentahydroxy-5-methoxy-(7Cl, 8Cl); 5-Methoxymyricetin; Myricetin 5-methyl ether 72 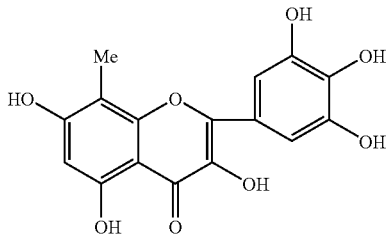

Formula: C16 H12 O8
CA Index Name: Flavone, 3,3',4',5,5',7-hexahydroxy-8-methyl-(8Cl)

73 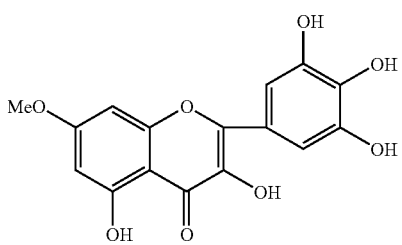

Formula: C16 H12 O8
CA Index Name: 4H-1-Benzopyran-4-one,3,5-dihydroxy-7-methoxy-2-(3,4,5-trihydroxyphenyl)-(9Cl)
Other Names: Flavone, 3,3',4',5,5'-pentahydroxy-7-methoxy-(8Cl); Europetin 74 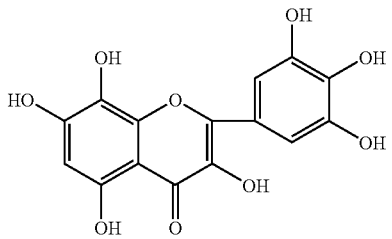

Formula: C15 H10 O9
CA Index Name: 4H-1-Benzopyran-4-one, 3,5,7,8-tetrahydroxy-2-(3,4,5-trihydroxyphenyl)-(9Cl)
Other Names: Flavone, 3,3',4',5,5',7,8-heptahydroxy-(8Cl; Hibiscetin (6Cl)

TABLE 1-continued

Some exemplary structures of myricitrin derivatives

Structure

75
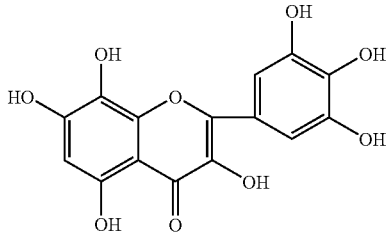

Formula: C16 H12 O8
CA Index Name: 4H-1-Benzopyran-4-one, 3,5,7-
trihydroxy-6-methyl-2-(3,4,5-trihydroxyphenyl)-(9CI)
Other Names: Flavone, 3,3',4',5,5',7-hexahydroxy-6-
methyl-(6CI, 8CI); 6-Methylmyricetin; Pinomyricetin 76
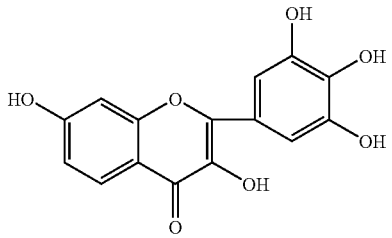

Formula: C15 H10 O7
CA Index Name: 4H-1-Benzopyran-4-one, 3,7-dihydroxy-2-
(3,4,5-trihydroxyphenyl)-(9CI)
Other Names: Flavone, 3,3',4',5',7-pentahydroxy-(8CI); Robinetin
(6CI); 3,3',4',5',7-Pentahydroxyflavone; 3,7,3',4',5'-
Pentahydroxyflavone; NSC 407331; NSC 656274; Norkanugin 77
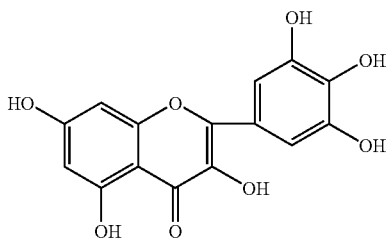

Formula: C15 H10 O8
CA Index Name: 4H-1-Benzopyran-4-one, 3,5,7-
trihydroxy-2-(3,4,5-trihydroxyphenyl)-(9CI)
Other Names: Flavone, 3,3',4',5,5',7-hexahydroxy-(8CI);
3,3',4',5,5',7-Hexahydroxyflavone; 3,5,7,3',4',5'-
Hexahydroxyflavone; Cannabiscetin; Myricetin;
Myricetol; NSC 407290

TABLE 1-continued

Some exemplary structures of myricitrin derivatives

Structure

78
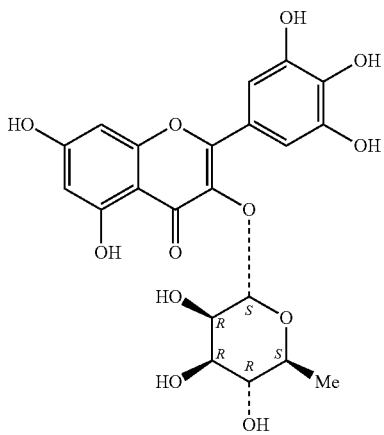

Absolute stereochemistry
Formula: C21 H20 O12
CA Index Name: 4H-1-Benzopyran-4-one, 3-[(6-deoxy-α-L-
mannopyranosyl)oxy]-5,7-dihydroxy-2-(3,4,5-trihydroxyphenyl)-
(9CI)
Other Names: Myricitrin (6CI, 7CI, 8CI); 3,3',4',5,5',7-
Hexahydroxyflavone, 3-rhamnoside; Myricetin 3-O-α-L-
rhamnopyranoside; Myricetin 3-O-α-L-rhamnoside; Myricetin 3-O-
α-rhamnopyranoside; Myricetin 3-O-rhamnoside; Myricetin 3-
rhamnoside; Myricitrine; Myricitroside; NSC 19803

In some embodiments, the composition described herein specifically exclude myricetin (FIG. 1B) or a derivative thereof. In some other embodiments, the composition described herein may specifically include myricetin and/or a derivative thereof.

In still some other embodiments, the composition described herein can include a mixture of at least two of the various compounds described above. For example, the composition may include myricetin (FIG. 1B) and myricitrin (FIG. 1A) and/or any of other compounds of formulae I, II, and IV described above. Compounds of formula II include compounds of formulae IIa, IIb, IIc, IId, and IIe and compounds as described in Table 1.

Formulation Carriers

The composition described herein may be administered to a subject in need of treatment by a variety of routes of administration, including orally and parenterally, (e.g., intravenously, subcutaneously or intramedullary), intranasally, as a suppository or using a "flash" formulation, i.e., allowing the medication to dissolve in the mouth without the need to use water, topically, intradermally, subcutaneously and/or administration via mucosal routes in liquid or solid form. The composition can be formulated into a variety of dosage forms, e.g., extract, pills, tablets, microparticles, capsules, oral liquid.

There may also be included as part of the composition pharmaceutically or physiologically acceptable compatible binding agents, and/or adjuvant materials. The active materials can also be mixed with other active materials including antibiotics, antifungals, other virucidals and immunostimulants which do not impair the desired action and/or supplement the desired action.

In one embodiment, the mode of administration of the composition described herein is oral. Oral compositions generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. In general, an effective dosage for myricitrin or a derivative thereof, e.g., compounds of Formulae I or III, described above, is in the range of 0.01 mg/kg/day to 100 mg/kg/day, preferably 0.01 mg/kg/day to 50 mg/kg/day in single or divided doses. Some variation in dosage will necessarily occur, however, depending on the condition of the subject being treated. These preparations should produce a serum concentration of active ingredient of from about 0.01 nM to 1,000,000 nM, e.g., from about 0.2 to 40 µM. A preferred concentration range is from 0.2 to 20 µM and most preferably about 1 to 10 µM. However, the concentration of active ingredient in the drug composition itself depends on bioavailability of the drug and other factors known to those of skill in the art.

In another embodiment, the mode of administration of the compositions described herein is topical or mucosal administration. A specifically preferred mode of mucosal administration is administration via female genital tract. Another preferred mode of mucosal administration is rectal administration.

Various polymeric and/or non-polymeric materials can be used as adjuvants for enhancing mucoadhesiveness of the composition disclosed herein. The polymeric material suitable as adjuvants can be natural or synthetic polymers. Representative natural polymers include, for example, starch, chitosan, collagen, sugar, gelatin, pectin, alginate, karya gum, methylcellulose, carboxymethylcellulose, methylethylcellulose, and hydroxypropylcellulose. Representative synthetic polymers include, for example, poly(acrylic acid), tragacanth, poly(methyl vinylether-co-maleic anhydride), poly(ethylene oxide), carbopol, poly(vinyl pyrrolidine), poly(ethylene glycol), poly(vinyl alcohol), poly(hydroxyethylmethylacrylate), and polycarbophil. Other bioadhesive materials available in the art of drug formulation can also be used (see, for example, Bioadhesion—Possibilities and Future Trends, Gurny and Junginger, eds., 1990).

It is to be noted that dosage values also varies with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The formulation may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. Materials used in preparing these various compositions should be pharmaceutically or physiologically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The compositions of the present invention are prepared as formulations with pharmaceutically or physiologically acceptable carriers. Preferred are those carriers that will protect the active compound against rapid elimination from the body, such as a controlled release formulation, including implants and microencapsulated delivery systems. Biodegradable, biocompatible polymers can be used, such as polyanhydrides, polyglycolic acid, collagen, and polylactic acid. Methods for preparation of such formulations can be readily performed by one skilled in the art.

Liposomal suspensions (including liposomes targeted to infected cells with monoclonal antibodies to viral antigens) are also preferred as pharmaceutically or physiologically acceptable carriers. Methods for encapsulation or incorporation of compounds into liposomes are described by Cozzani, I.; Jori, G.; Bertoloni, G.; Milanesi, C.; Sicuro, T. Chem. Biol. Interact. 53, 131-143 (1985) and by Jori, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15(1), 67-70 (1987) and Jori, G.; Reddi, E.; Cozzani, I.; Tomio, L. Br. J. Cancer, 53(5), 615-21 (1986).

The composition described herein may be administered in single (e.g., once daily) or multiple doses or via constant infusion. The compounds of this invention may also be administered alone or in combination with pharmaceutically or physiologically acceptable carriers, vehicles or diluents, in either single or multiple doses. Suitable pharmaceutical or physiologically carriers, vehicles and diluents include inert solid diluents or fillers, sterile aqueous solutions and various organic solvents. The compositions described herein are then readily administered in a variety of dosage forms such as tablets, powders, lozenges, syrups, injectable solutions and the like. These pharmaceutical compositions can, if desired, contain additional ingredients such as flavorings, binders, excipients and the like according to a specific dosage form.

Thus, for example, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical/physiological agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

The composition provided herein can also be used with another pharmaceutically or physiologically active agent effective for a disease such as neurodisorders, cardiovascular disorders, tumors, AIDS, depression, and/or type-1 and type-2 diabetes. Such additional agents can be, for example, antiviral agent, antibiotics, anti-depression agent, anti-cancer agents, immunosuppressant, anti-fungal, and a combination thereof.

The composition described herein can be formulated alone or together with the other agent in a single dosage form or in a separate dosage form. Methods of preparing various formulations with a certain amount of active ingredient are known, or will be apparent in light of this disclosure, to those skilled in this art. For examples of methods of preparing pharmaceutical formulations, see Remington's Pharmaceutical Sciences, Mack Publishing Company, Easton, Pa., 19th Edition (1995).

Methods of Use

The composition described herein can be used for treating, preventing or ameliorating the above described conditions in a mammal, including a human. The composition can be administered as part of an appropriate dosage regimen designed to obtain the benefits of the therapy. The appropriate dosage regimen, the amount of each dose administered and the intervals between doses of the compound will depend upon the compound of Formulae I, II or IV of this invention being used, the type of pharmaceutical compositions being used, the characteristics of the subject being treated and the severity of the conditions.

The compounds of Formulae I, II or IV of the present invention are useful for the treatment of insomnia, depression-related disease, stress-related disease, depression-related sleep disorder, and neurodegeneration diseases such as Alzheimer's disease, Pick's disease, spinocerebellar degeneration, Parkinson's disease, chorea, glaucoma, amyotrophic lateral sclerosis, senile macular degeneration, hepatic encephalopathy, demyelinating diseases, Lewy body dementia, multi-infarct dementia, multiple sclerosis.

The term "depression-related disease" means a disease caused by an abnormally low serotonin level in the synapse. Examples of such a disease include seasonal affective disorder, premenstrual syndrome, unipolar depression, bipolar depression, manic-depressive psychosis and atypical depression and depression-related sleep-disorder.

The "stress-related disease" is also caused by an abnormally low serotonin level, and examples thereof include depression, posttraumatic stress disorder, stress-related bodily disorders like idiopathic pain syndromes and chronic fatigue syndrome.

The term "depression-related sleep disorder" means a sleep disorder which is caused by dysfunction of the serotonin and melatonin system. Examples of such a disease include insomnia, hypersomnia, parasomnia, dysomnia, fibromyalgia, jetleg, shift-work sleep disorder, delayed-sleep phase syndrome, and advanced-sleep phase syndrome.

The term "neurodegeneration disease" refers to a disorder in which neuro degeneration is involved. Examples of such a disease include Alzheimer's disease, Pick's disease, spinocerebellar degeneration, Parkinson's disease, chorea, glaucoma, amyotrophic lateral sclerosis, senile macular degeneration, hepatic encephalopathy, demyelinating diseases, Lewy body dementia, multi-infarct dementia, multiple sclerosis.

Methods of Making Myricitrin and Related Compounds

Myricitrin is a plant flavinoid found in numerous herbs such as; witch hazel (Hamameliadaceae *hamamelis Virginia*); bayberry (*Myrica cerifera*); *Corylus avellana* L. and Myrtaceae and can be readily isolated from a plant or herb such as the ones listed below in Table 2.

TABLE 2

| List of plants containing myricitrin | |
|---|---|
| Species | Part |
| *Araucaria bidwillii* HOOK. [Araucariaceae] | Plant |
| *Ardisia japonica* L. [Myrsinaceae] | Leaf |
| *Caesalpinia pulcherrima* (L.) SW. [Fabaceae] | Plant |
| *Catha edulis* VAHL [Celastraceae] | Plant |
| *Corylus avellana* L. [Betulaceae] | Leaf |
| *Corylus avellana* L. [Betulaceae] | Bark |
| *Juglans nigra* L. [Juglandaceae] | Fruit |
| *Liquidambar styraciflua* L. [Hamamelidaceae] | Leaf |
| *Myrica cerifera* L. [Myricaceae] | Plant |
| *Myrtus communis* L. [Myrtaceae] | Plant |
| *Ononis spinosa* L. [Fabaceae] | Shoot |
| *Rhus coriaria* L. [Anacardiaceae] | Leaf |
| *Desmanthus illinoensis* [Family: Fabaceae (bean family); subfamily: Mimosoideae (mimosa) | |
| *Arctostaphylos uva ursi* (also known as *Uvae ursi folium*, *Arctostaphylos*, bearberry, and beargrape) | |
| *Polygonum aviculare* | |
| *Herba Ardisiae JaPonicae* | |
| *Cotinus coggygria* Scop. var. *cinerea* Engl. [Anacardiaceae] | |
| Witch Hazel *Hamamelis virginiana* [Hamameliadaceae] | |

Myricitrin derivatives can be synthesized via methods known in the art of medicinal chemistry and/or organic synthesis (see, for example, Rolf Carlson, Design and Optimization in Organic Synthesis, Elsevier; W. A. Smit, et al., The Science behind The Art, 1998).

Some representative methods of making compounds of formulae I, II or IV are provided in the schemes shown in FIGS. 2-5 (see also, Journal of Natural Products, 64(4), 462-465 (2001); Khimiya Prirodnykh Soedinenii, (2), 274-6 (1990); Zhiwu Xuebao, 31(3), 205-8 (1989); Chemical & Pharmaceutical Bulletin, 50(6), 788-795 (2002); and Perkin 2 (9), 1946-1952 (2000)).

The following non-limiting examples illustrate a few embodiments of the present invention.

EXAMPLES

Example 1

Effects of Mixtures of Dihydromyricetin, Myricetin and Myricitrin on Loss of Righting Reflex in Male C57/B6 Mice C57/B6 mice were randomised into groups and orally administered. Compound mixtures-1, -2, -3 (Table 3), which are mixtures of dihydromyricetin (compound A), myricetin (compound B) and myricitrin (compound C), or vehicle 60 min prior to low dose injection of sodium pentobarbitone (12.5 mg/kg, i.p.).

TABLE 3

Compound mixture compositions

| Compound Mixture-1: | 90.38% A | 7.77%B | 1.84% C |
| Compound Mixture-2: | 95.14% A | 3.69%B | 1.23% C |
| Compound Mixture-3: | 75.46% A | 23.26%B | 1.27% C |

Figure 6:
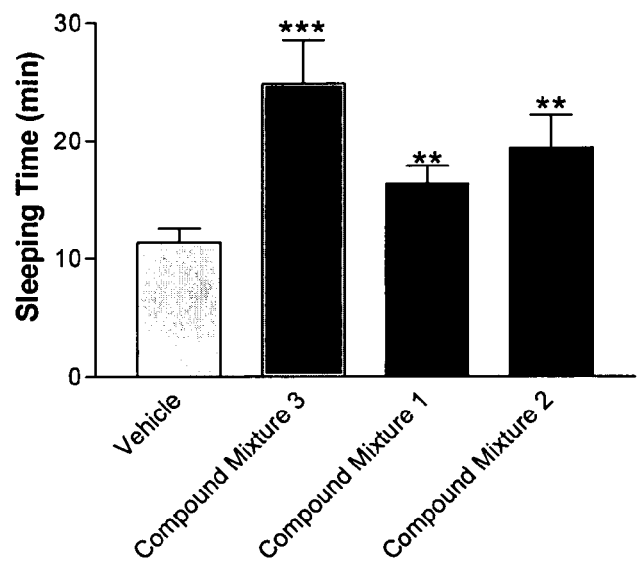
FIG. 6 shows effects of mixtures of dihydromyricetin, myricetin and myricitrin on loss of righting reflex in male C57/B6 mice.

The animals were then placed on a heating pad (37° C.) and their duration of sleep was then determined according to loss of righting reflex. FIG. 6 shows loss of righting reflex in male C57/B6 mice following oral treatment of compound mixtures-1, -2 and -3 (50 mg/kg, p.o.) versus vehicle (10 ml/kg, $H_2O$, p.o), 1 hour prior to pentobarbital (12.5 mg/kg, i.p.) injection. Data were analysed by unpaired t-test versus vehicle treated group ( p<0.01, * p<0.001, n>11).

These test results demonstrated that all extracts containing different ratios of compounds A, B and C were able to significantly prolong pentobarbital induced-sleeping time, with compound mixture-3 having the greatest effect (FIG. 6). The results seem to be reflective of the ratios of the active compounds within each mixture, with the extract containing almost equal balance of A and B (mixture-3) being most effective.

Example 2

Figure 7A:
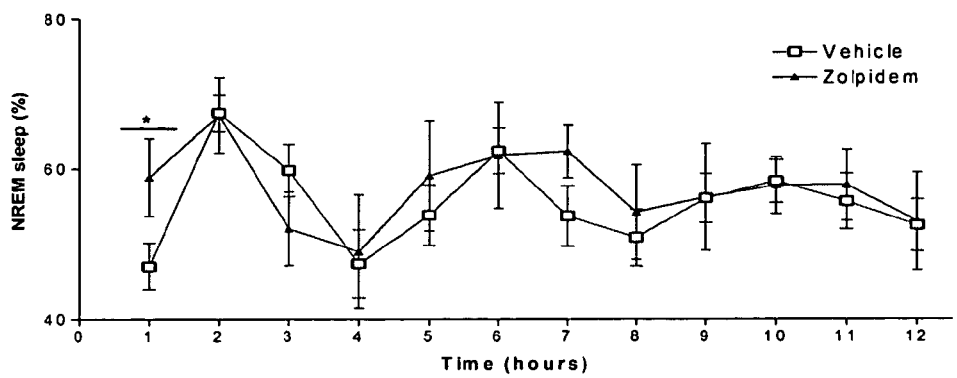
FIGS. 7A-7C shows the comparison of the effects of Compound Mixture, zolpidem and zopiclone versus vehicle treatment on sleep latency and quality.
Figure 7B:
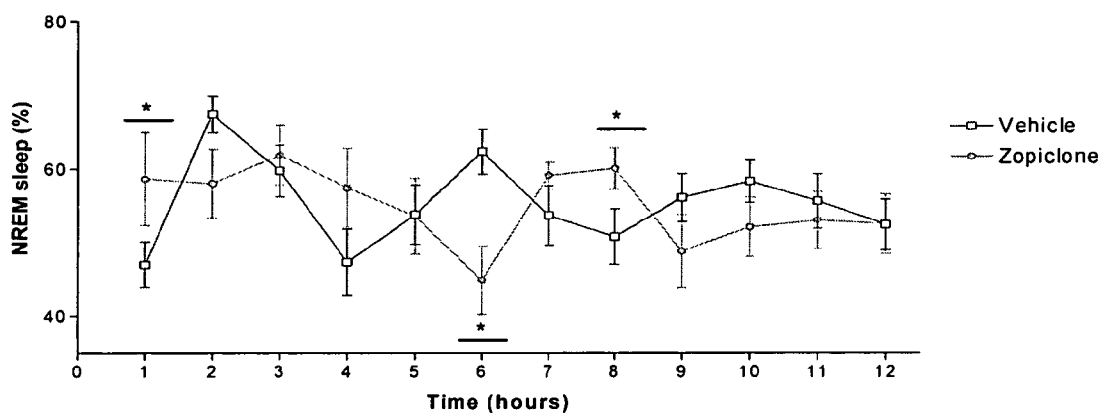
Figure 7C:
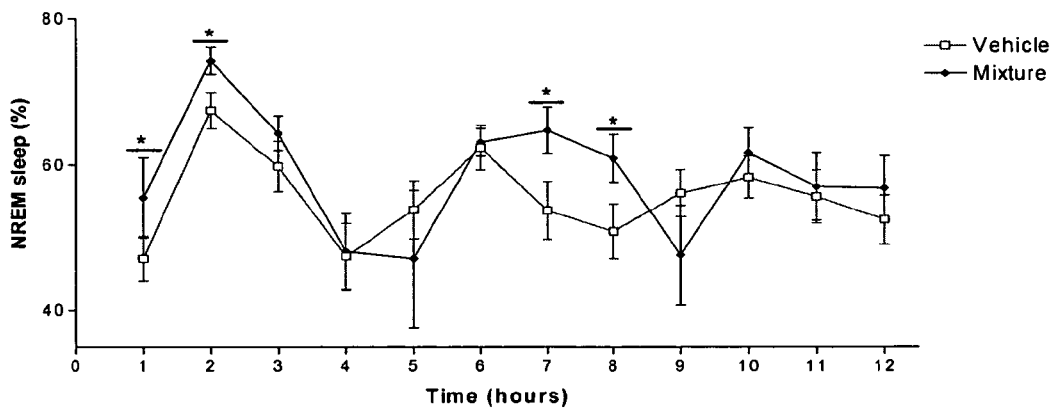

Telemetry Studies in Freely Moving Male Wistar Rats—Comparison of the Effects of Compound Mixture, Zolpidem and Zopiclone Versus Vehicle Treatment on Sleep Latency and Quality Telemetric EEG, activity and temperature monitors were surgically implanted sub-coetaneously onto the lower backs of male Wistar rats, under ketamie and xyalsine (75/10 mg/kg, i.p.) anaesthesia. A skin incision was made above the scull and the transmitter tunnelled subcutaneously from the neck to the lower back with blunted scissors. The EEG leads were placed into two 0.5 mm holes that were drilled stereotaxically 2 mm anterior to Lambda and 1 mm to the left and right of centre, so that contact was made with the durra, and fixed with quick drying glue and reinforced with dental cement. The incision was then closed with 4-0 silk suture and post operative temgesic applied for pain relief. Following a 4 week recovery and acclimatization period in individually housed ventilated cages (12 hour light/12 hour dark cycle 20-25° C.), the rats were orally treated with either test compounds, positive controls or vehicle 45-30 min prior commencement of their light cycle (sleeping period). A Latin square dosing regiment was used where each rat received each of the drugs tested in random order with 4 days clearance time between each dosing. EEG waveforms were analysed using a power spectral analysis of each 5 second epoch and scored manually into % duration of NREM sleep for each hour over a 12 hour period. FIGS. 7A-7C shows the duration of NREM sleep induced by zolpidem (5 mg/kg, p.o., FIG. 7A), zopiclone (5 mg/kg, p.o., FIG. 7B) or Compound Mixture (50 mg/kg, p.o., FIG. 7C), which is a mixture of dihydromyricetin (compound A), myricetin (compound B) and myricitrin (compound C) (A/B/C=1:0.1:0.08) in male Wistar rats during 12-hour light cycle. Data were analysed using Two-way ANOVA versus vehicle treatment (*p<0.05, n=7).

As shown in FIGS. 7A-7C, zolpidem (5 mg/kg, p.o., FIG. 7A), Zopiclone (5 mg/kg,p.o., FIG. 7B) and the Compound Mixture (FIG. 7C) all significantly increased NREM sleep within the first hour following treatment, indicating that they were able to significantly reduce sleep latency compared to vehicle treatment. During the second hour following treatment, compound mixture (FIG. 7C) continued to maintain long durations of NREM sleep, whereas zolpidem and zopiclone (FIGS. 7A and 7B) were not significantly different from vehicle treatment. During the remainder of the sleep period, zolpidem (FIG. 7A) failed to significantly improve NREM sleep compared to vehicle, whereas zopiclone (FIG. 7B) only significantly improved NREM sleep duration during the $8^{th}$ hour, but had a negative effect on sleep quality during the $6^{th}$ hour of sleep. Conversely, Compound Mixture (FIG. 7C) was also able to significantly improve NREM sleep during the $7^{th}$ and $8^{th}$ hour of sleep and had no observed detrimental effect on NREM duration during the course of the sleep period.

Further tests showed that compound mixtures of A:B:C in the ratios of 1-2:0.1-0.12:0.05-0.08 all showed similar results in telemetry rats.

The present data indicate that the Compound Mixture is able to significantly reduce sleep latency with a similar effect to existing sedatives zolpidem and zopiclone in rats. Furthermore the Compound Mixture is able to maintain longer periods of NREM sleep during the sleep period and thus attain a deeper sleep than both zolpidem and zopiclone, indicating that the Compound Mixture may be beneficial for improving the quality of sleep.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A composition comprising dihydromyricetin, myricetin, and myricitrin in a weight percentage ratio selected from the group consisting of 90.38:7.77:1.84, 95.14:3.69:1.23, and 75.46:23.26:1.27.

2. The composition of claim 1, wherein the weight ratio is 75.46:23.26:1.27.

3. The composition of claim 1, further comprising a pharmaceutically acceptable carrier.

4. The composition of claim 3, wherein the pharmaceutically acceptable carrier is a carrier suitable for oral delivery, parenteral delivery, topical delivery, mucosal delivery, intradermal delivery, intravenous injection, subcutaneous injection, intramedullary injection, administration by inhalation, and intranasal delivery.

5. The composition of claim 1 in a dosage form selected from the group consisting of a solution, a suspension, a syrup, a tablet, a capsule, microparticles, an ointment, a cream, and a lozenge.

6. The composition of claim 1, which is a pharmaceutical composition.

7. The composition of claim 1, which is a nutraceutical composition or dietary supplement composition.

* * * * *